United States Patent [19]

Mathur et al.

[11] Patent Number: 5,260,065
[45] Date of Patent: Nov. 9, 1993

[54] BLENDED LIPID VESICLES

[75] Inventors: Rajiv Mathur, Nashua; Donald F. H. Wallach, Hollis, both of N.H.

[73] Assignee: Micro Vesicular Systems, Inc., Nashua, N.H.

[21] Appl. No.: 761,253

[22] Filed: Sep. 17, 1991

[51] Int. Cl.$^5$ ............................................. A61K 9/127
[52] U.S. Cl. ................................ 424/450; 428/402.2
[58] Field of Search ............... 424/450, 417; 436/829; 428/402.2

[56] References Cited

U.S. PATENT DOCUMENTS

| | | | |
|---|---|---|---|
| 3,069,370 | 12/1962 | Jensen et al. | 260/23 |
| 3,372,201 | 5/1968 | Leary et al. | 260/615 |
| 3,957,971 | 5/1976 | Oleniacz | 424/70 |
| 4,075,131 | 2/1978 | Sterling | 252/542 |
| 4,182,330 | 10/1980 | Michaels | 128/260 |
| 4,235,871 | 11/1980 | Papahadjopoulos et al. | 424/19 |
| 4,241,046 | 12/1980 | Papahadjopoulos | 424/19 |
| 4,247,411 | 1/1981 | Vanlerberghe et al. | 252/316 |
| 4,271,344 | 8/1981 | Vanlerberghe et al. | 424/60 |
| 4,348,329 | 9/1982 | Chapman | 268/483 |
| 4,356,167 | 10/1982 | Kelly | 424/38 |
| 4,377,567 | 3/1983 | Geno | 424/1 |
| 4,536,324 | 8/1985 | Fujiwara | 252/311 |
| 4,544,545 | 10/1985 | Ryan et al. | 424/1.1 |
| 4,551,288 | 11/1985 | Kelly | 264/4.6 |
| 4,610,868 | 9/1986 | Fountain et al. | 424/1.1 |
| 4,666,711 | 5/1987 | Vanlerberghe et al. | 424/70 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,762,915 | 8/1988 | Kung et al. | 530/405 |
| 4,772,471 | 9/1988 | Vanlerberghe et al. | 424/450 |
| 4,789,633 | 12/1988 | Huang et al. | 435/240 |
| 4,832,872 | 5/1989 | Scandel | 252/547 |
| 4,855,090 | 8/1989 | Wallach | 264/4.1 |
| 4,897,308 | 1/1990 | Vanlerberghe et al. | 428/402 |
| 4,911,928 | 3/1990 | Wallach | 424/450 |
| 4,917,951 | 4/1990 | Wallach | 428/402 |
| 5,019,392 | 5/1991 | Wallach | 424/420 |
| 5,021,200 | 6/1991 | Vanlerberghe et al. | 264/4.3 |
| 5,032,457 | 7/1991 | Wallach | 428/402 |

FOREIGN PATENT DOCUMENTS

| | | |
|---|---|---|
| 0032578 | 7/1981 | European Pat. Off. |
| 0167825 | 1/1986 | European Pat. Off. |
| 59-106423 | 6/1984 | Japan . |
| 61-207324 | 9/1986 | Japan . |
| 8706499 | 5/1987 | PCT Int'l Appl. |
| 1539625 | 1/1979 | United Kingdom . |
| 2078543 | 1/1982 | United Kingdom . |
| 2079179 | 1/1982 | United Kingdom . |
| 2147263 | 5/1985 | United Kingdom . |
| 2166107 | 4/1986 | United Kingdom . |

OTHER PUBLICATIONS

McCuthcheon, "Detergents and Emulsifiers", No. American Edition (1973).
*Biochimica et Biophysica Acta*, 684 (1982) 149–153.
Murahami et al., J. Org. Chem. 47:2137–2144 (1982).
Gregoriadis, N. E. J. Med. 13:704–710 (1976).
Bangham et al. J. Mol. Biol. 13:238–252 (1965).
Szoha et al., Proc. Nat'l. Acad Sci. USA 75:4194–4198 (1978).
Baillie et al., J. Pharm. Pharmacol. 37:863–868 (1985).
Puisieux et al., "Problemes Technologiques Poses Par L'utilisation des Liposomes . . ." (1985).
Baille et al., J. Pharm. Pharmacol 38:502–505 (1986).
Dousset et al., "Methods de Preparation des Liposomes . . ." (1985).
Ribier et al., Colloids and Surfaces 10:155–161 (1984).

*Primary Examiner*—Thurman K. Page
*Assistant Examiner*—G. Kishore

[57] ABSTRACT

A new class of lipid vesicles having a blend of two lipids, a primary lipid and a secondary lipid, has been developed. The primary lipid, which forms the greatest proportion of lipid by weight, will not form vesicles nor preferably, even a lamellar phase, without addition of the secondary lipid. Preferably primary lipids are $C_{12}$–$C_{18}$ fatty alcohols, $C_{12}$–$C_{18}$ glycol monoesters, and $C_{12}$–$C_{18}$ glyceryl mono- and diesters.

9 Claims, No Drawings

BLENDED LIPID VESICLES

BACKGROUND OF THE INVENTION

The present invention relates to the formation of lipid vesicles, e.g., paucilamellar lipid vesicles, using blended lipids. These vesicles have as the major lipid a waxy or oily material which, in an unblended state, forms neither a lamellar phase nor vesicles. More particularly, waxy or oily materials such as fatty alcohols, glyceryl mono- and diesters of long-chain fatty acids, and glycol monoesters are used, in combination with other materials which may or may not form lamellar phases or vesicles, to form stable vesicles. These vesicles are particularly useful for cosmetic and pharmaceutical applications.

U.S. Pat. No. 4,911,928, discusses a broad variety of materials which may be used to form oil-filled lipid vesicles. All of the materials discussed in the aforementioned patent, the disclosure of which is incorporated herein by reference, will form vesicles by themselves when hydrated. However, certain additives, like charge-producing agents or sterols such as cholesterol, may be included in the vesicular structure. U.S. Pat. No. 4,917,951, the disclosure of which is also incorporated herein by reference, discloses a class of materials which cannot form vesicles unless a sterol such as cholesterol is added. However, all of the materials described in both of these patents, as well as the patents cited therein such as the Vanlerberghe U.S. Pat. No. 4,217,344, concerning materials which form vesicles without the addition of a second structural lipid. In fact, many of these materials may be able to form a lamellar phase under proper conditions, as described in the Vanlerberghe U.S. Pat. No. 4,217,344.

However, many cosmetic preparations include compounds which form neither vesicles nor a lamellar phase. These include the $C_{12}$–$C_{18}$ fatty alcohols (which are used to provide "feel" to certain cosmetics), glycol stearate a common thickener), glyceryl mono- and distearate (which are used as emulsifiers), and glyceryl dilaurate (which is often used in dermatologicals). Since cosmetics and dermatologicals are one of the most rapidly expanding fields for the use of lipid vesicles, it would be logical to attempt to use as the vesicle formers amphiphiles which are commonly incorporated in the cosmetics. However, these amphiphiles cannot be made into vesicles using either using conventional techniques, or even those techniques described in U.S. Pat. No. 4,911,928. These materials are either water soluble so that they cannot form vesicles or a lamellar phase, or they are so oily or waxy that they can only be formed into emulsions, e.g., they do not hydrate sufficiently well for vesicle formation. In fact, these materials do not form vesicles even with standard additives such as cholesterol or charge-producing agents.

Accordingly, an object of the invention is to provide a method of making lipid vesicles using as a primary or major structural lipid of the bilayers a lipid which will not form vesicles in an unblended state.

Another object of the invention is to provide lipid vesicles having two or more lipids blended to form the lipid bilayers, at least one of which will not form a lamellar phase or vesicles in an unblended state.

A further object of the invention is to provide a method of forming lipid vesicles using cosmetic, pharmaceutical, or dermatologically useful substances as the primary vesicle formers.

These and other objects and features of the invention will be apparent from the following description.

SUMMARY OF THE INVENTION

The present invention features lipid vesicles and a method of manufacture using a blend of at least two lipids or amphiphiles in forming the bilayers. Neither of these lipids is a sterol such as cholesterol nor is the primary lipid charged. At least the primary and, in many cases, all of the lipids which constitute the bilayer structure form neither lamellar phases nor vesicles in an unblended state. Preferably, the desaturation and chain lengths of the lipids are matched, e.g., $C_{16}$ with $C_{16}$, to provide a good structural fit. These vesicles feature materials with special usefulness for cosmetic and dermatological processes and products.

The vesicles in the invention have a primary lipid selected from the group consisting of $C_{12}$–$C_{18}$ fatty alcohols, $C_{12}$–$C_{18}$ glycol monoesters, $C_{12}$–$C_{18}$ glyceryl mono- and diesters mixtures thereof. The term "primary lipid" as used herein means and implies that the lipid constitutes the greatest proportion (by weight) of any single lipid material forming the lipid bilayers, preferably 60% or greater. Preferred primary lipids are $C_{16}$ and $C_{18}$ fatty alcohols, glycol stearate, glyceryl monostearate, glyceryl distearate, and glyceryl dilaurate. None of these materials will form vesicles or lamellar phases on their own. However, vesicles can be formed when these materials are blended with another amphiphile, which may or may not form vesicles or a lamellar phase on its own, and then hydrated. Preferred other amphiphiles have like chain length and unsaturation but some variations are acceptable. The term "like chain length and unsaturation," as used herein, means and implies that both materials would have identical fatty acid chains, e.g., both stearate rather than a stearate and oleate or stearate and laurate. This other amphiphile, designated herein the "secondary lipid," is preferably selected from the group consisting of quaternary dimethyldiacyl amines (includes ammonium derivatives such as chlorides), polyoxyethylene acyl alcohols, polyglycerols fatty acids, and sorbitan fatty acid esters (trade name SPAN). In certain circumstances, a sterol such as cholesterol, a cholesterol salt or ester, phytocholesterol, or hydrocortisone may also be added.

The vesicles of the invention may be used to encapsulate a large number of water immiscible oily or waxy materials. The basic requirement for these water immiscible oily or waxy materials are that they are both highly water immiscible and highly immiscible in the lipids used to form the bilayers. Examples of these water immiscible oily or waxy materials include mineral oils, paraffin waxes, petrolatum, triglyceride oils and fats, perfumes and fragrances, flavor oils, water insoluble vitamins, perfluorocarbon liquids, and a variety of water immiscible solvents. Of particular interest is the encapsulation of anthralin or retinoic acid as the water immiscible material. These materials provides pharmacological or dermatological benefits in addition to the benefits caused by the use of the particular primary and secondary lipids. Paucilamellar lipid vesicles having the water immiscible material in the amorphous central cavity can be obtained.

Oil filled vesicles, e.g., vesicles having their amorphous central cavities substantially filled with a water immiscible oily material, may be formed using either the "hot loading" technique disclosed in U.S. Pat. No. 4,911,928 or the "cold loading" technique described in U.S. Pat. application Ser. No. 598,120, the disclosure of which is also incorporated herein by reference. In either case, the primary lipid and, if lipid soluble, the secondary lipid are blended (preferably at elevated temperature) together with any sterol and other lipophilic additives, if any, that are added. An aqueous phase is formed by heating the hydration liquid, e.g., water, saline, or any other aqueous solution which will be used to hydrate the lipid, and aqueous soluble material to be incorporated into the vesicle. If an aqueous soluble amphiphile is used as the secondary lipid, it is added to the aqueous phase. A third phase, a water immiscible phase, is formed of the water immiscible oily liquid to be incorporated into the vesicles and any other materials which are soluble therein. When the "cold loading" technique is used, the aqueous phase and the lipid phase are then blended under shear mixing conditions to form vesicles. "Shear mixing conditions," as used herein, means a shear equivalent to a relative flow of 5–50 m/s through a 1 mm orifice. The vesicles formed are paucilamellar lipid vesicles having amorphous central cavities filled with the aqueous hydrating solution. These vesicles can then be "cold loaded" with the water immiscible phase using the techniques described in the aforementioned U.S. Pat. application Ser. No. 598,120.

If a "hot loading" technique is used, the water immiscible phase is blended with the lipophilic phase prior to hydration by the aqueous phase of the combined lipophilic/water immiscible phase under the shear mixing conditions. Using either technique, the vesicles formed can have high oil content in their amorphous central cavities.

All the materials described in conjunction with the products may be used in the methods of these inventions. Other modifications of the methods and products will be apparent from the following description and the claims.

DETAILED DESCRIPTION OF THE INVENTION

The present invention uses a blend of lipid amphiphiles to form vesicles. In particular, the primary lipid, a lipid which will not form a lamellar phase or vesicles on its own, is blended with a secondary lipid to form a combination which can be hydrated to form a vesicle. Other additives such as a sterol or a charge-producing agent may also be added.

The preferred primary lipids are $C_{12}$-$C_{18}$ fatty alcohols, glyceryl mono- and distearate, glyceryl dilaurate, and glycol stearate. While any of the secondary lipids could be used with any of the primary lipids, preferred combinations include polyoxyethylene 10–20 acyl alcohols or quaternary dimethyldiacyl amines as the secondary lipids to be used in conjunction with the fatty alcohols. Matching chain lengths in terms of carbon content and unsaturations is an important factor to consider for selection of the secondary lipid. These same acyl alcohols and dimethyldiacyl (specifically distearyl) amines are also useful with the glycol stearate, glyceryl monostearate, glyceryl distearate and the glyceryl dilaurate. However, the glyceryl distearate and glyceryl dilaurate may also use sodium laurate sarcosinates, as well as other matching sarcosinate salts (all being water soluble), or lauryl sarcosinates as secondary lipids.

In certain instances, primarily the stearate derivatives, a sterol such as cholesterol is a particularly useful additive. The addition of cholesterol appears to make the vesicles population more uniform in terms of size and shape.

Even cholesterol is not sufficient, in itself, to allow vesicle formation. This is contrast to the materials described in U.S. Pat. No. 4,917,951 which only require cholesterol to make vesicles. In certain circumstances, cholesterol will allow these materials which will not otherwise form a lamellar phase to form a lamellar phase but they cannot be formed into vesicles without the addition of the secondary lipid. In fact, some of the most preferred secondary lipids, e.g., dimethyldistearyl amine, water soluble polyoxyethylene acyl alcohols, and acyl sarcosinate salts, will not form vesicles or lamellar phases either.

The following Examples will clearly illustrate the efficacy of the invention.

Example 1

In this Example, a variety of materials were blended in order to make vesicles. Table 1 shows the composition, water uptake level, and oil uptake under hot and cold loading techniques of five different compositions. None of the primary lipids used, e.g., glyceryl dilaurate (GDL), glyceryldistearate (GDS), cetyl alcohol (CA), stearyl alcohol (SA), or glycol stearate (GS) will form vesicles or lamellar phase on their own.

TABLE 1

| Composition | Water Uptake (ml/ml) | Oil Uptake (ml/ml) | |
|---|---|---|---|
| | | Hot | Cold |
| GDL/C16Q/Chol (1.0/0.05/0.05) | 13.5 | ≧7.2 | ≧2.7 |
| GDS/POE10SA/Chol (1.0/0.5/0.25) | 12.5 | ≧6.5 | ≧6.5 |
| CA/POE10CA/Chol (1.0/0.2/0.1) | 9.5 | ≧4.2 | ≧4.2 |
| SA/C18Q/Chol (1.0/0.2/0.1) | 13.5 | ≧6.5 | ≧6.5 |
| GS/POE10SA/Chol (1.0/0.2/0.1) | 13.5 | ≧6.5 | ≧6.5 |

The first compound shown in Table 1 is a blend of glyceryl dilaurate, dimethyldicetyl quaternary amine (C16Q), and cholesterol (Chol) in a 1.0:0.05:0.05 molar ratio. The water uptake is 13.5 ml/ml of lipid and the hot load and cold loading values were ≧7.2 and ≧2.7 ml of oil/ml of lipid, respectively. The vesicles were made by blending the two lipids and the cholesterol at 70°–75° C. with the aqueous phase at 65° C. The lipid phase was placed in one syringe, the aqueous phase was placed in another syringe, and the two syringes were connected by a stopcock. The material was shear mixed by blending from one syringe to another through the stopcock forming vesicles in less than two minutes. For the cold loading technique, the preformed vesicles were mixed with 20% and 50% V/V mineral oil (Drakeol 19) using the same syringe technique to load the oil. For the hot loading technique, the oil was heated to 70°–75° C., blended with the lipophilic phase prior to hydration by the aqueous phase, and then the combined lipophilic/water immiscible oily phase was hydrated by the aqueous phase. Either hot loading or cold loading techniques may be used for a mineral oil but with a highly volatile oil which would not survive the 70°–75° C. heating, the cold loading technique, which can be carried out a ambient temperature, is preferred.

The second compounded tested was a blend of glyceryl distearate, Polyoxyethylene 10 stearyl alcohol (PO- E10SA), and cholesterol in a 1.0:0.5:0.25 molar ratio. This blended material had a water uptake of 12.5 ml/ml lipid and the oil uptake for either hot and cold loading was >6.5 ml/ml using the same techniques previously described.

The third material tested was a blend of cetyl alcohol, polyoxyethylene 10 cetyl alcohol (POE10CA), and cholesterol in a 1:0.2:0.1 molar ratio. Water uptake was 9.5 ml/ml and both hot and cold oil uptake was >4.2 ml/ml lipid.

The fourth combination tested was a blend of stearyl alcohol, dimethyldistearyl quaternary amine (C18Q), and cholesterol on a 1:0.2:0.1 ratio. Water uptake was 13.5 ml/ml and oil uptake on both a hot and cold basis was >6.5 ml/ml lipid.

The fifth compound tested was a blend of glycol stearate, polyoxyethylene 10 stearyl alcohol, and cholesterol in a 1:0.2:0.1 ratio. Again, the water uptake was approximately 13.5 ml/ml and the oil uptake was >6.5 ml/ml under both hot and cold loading techniques.

Example 2

In this Example, retinoic acid, a water insoluble material in a water immiscible carrier, was used in lieu of the mineral oil of Example 1 in the amorphous central cavity of the paucilamellar lipid vesicles. Retinoic acid has a substantial number of dermatological uses including, potentially, the reduction of facial wrinkles.

TABLE 2

|  | A | B |
|---|---|---|
| Cetyl Alcohol | 4.7 g |  |
| Glycol Stearate |  | 11.5 g |
| POE10 Cetyl Alcohol | 2.35 g |  |
| POE10 Stearyl Alcohol |  | 2.3 g |
| Cholesterol | 1.2 g | 1.15 g |
| Petrolatum | 10.9 g |  |
| Paraffin Wax | 11.6 g |  |
| Soybean Oil |  | 21.8 g |
| Retinoic Acid | 0.25 g | 0.25 g |
| Deionized Water | 69 g | 63 g |

Table 2 shows the formulas for two different retinoic acid formulations, one using a cetyl alcohol/polyoxyethylene 10 cetyl alcohol blend and the other using a glycol stearate/polyoxyethylene 10 stearyl alcohol blend as the vesicles formers. Both formulas include cholesterol while one uses a mixture petrolatum and paraffin wax as a carrier for the retinoic acid while the other uses a soybean oil carrier. In both cases, the retinoic acid was dissolved in the carrier at 65°-75° C. The lipids and the cholesterol were then heated and blended to homogeneity and the retinoic acid mixture was added and blended therein. An aqueous phase consisting of the deionized water was then heated to approximately 65° C. and the resulting phases were shear mixed to form the vesicles. While the syringe method described in Example 1 could be used, a NovaMix TM vesicle forming machine manufactured by Micro Vesicular Systems, Inc., Nashua, N.H. was used. This machine, which is described in more detail in U.S. Pat. No. 4,895,452, the disclosure of which is incorporated herein by reference, has a substantially cylindrical central chamber with an axial outflow tube and tangentially located inflow tubes. The phases are injected into the central chamber, under pressure sufficient to form turbulent flow and shear mixing, rapid vesicle formation occurs, and the vesicles are removed through the outflow tube.

These Example show that retinoic acid may be encapsulated within vesicles of the invention.

Example 3

In this Example, two different formulations for encapsulating anthralin, an antipsoriatic, were tested. Table 3 lists the ingredients used in these formulations.

TABLE 3

|  | C | D |
|---|---|---|
| Glyceryl Distearate | 9.4 g |  |
| Cetyl Alcohol |  | 6.85 g |
| Dimethyl Distearyl Ammonium Chloride | 0.3 g | — |
| POE10 Cetyl Alcohol |  | 1.35 g |
| Sodium Lauryl Sarcosinate | 1.4 g |  |
| Cholesterol | 1.0 g | 0.7 g |
| Petrolatum | 15.7 g | 17.3 g |
| Paraffin Wax | 16.8 g | 18.5 g |
| Anthralin | 0.5 g | 0.5 g |
| Deionized Water | 54.9 g | 54.8 g |

In formulation C, the petrolatum and paraffin are melted together and the anthralin is dissolved into the carrier mixture. This also the case of formulation D. This petrolatum/paraffin wax mixture appears to be particularly advantageous in that micro-crystals form rather than the macroscopic crystals which normally appear when anthralin cools. In formulation C, however, the glyceryl distearate, cholesterol and dimethyldistearyl ammonium chloride are blended together at approximately 75° C. until clear and the anthralin solution (forming a water immiscible phase) is then mixed therein. The aqueous phase is formed by heating the deionized water to approximately 65° C. and dissolving the secondary lipid, the sodium lauryl sarcosinate, therein. The aqueous phase and the lipid phase are then shear mixed, using a NovaMix TM machine as described in Example 2, to form vesicles. In contrast, in formulation D, the cetyl alcohol, polyoxyethylene 10 cetyl alcohol and the cholesterol are blended together at an elevated temperature, the anthralin solution is mixed in, and the aqueous which consists merely of the deionized water is shear mixed using the NovaMix TM machine to form the vesicles. The difference in the procedure is that the non-ionic lipids of formulation D cannot be carried in the aqueous solution as is the ionic sodium lauryl sarcosinate of formulation C. Either formulation forms acceptable anthralin carrying vesicles.

Example 4

In this Example, three different materials, Vitamin E acetate, levamisole base, and a butter flavor oil were carried in the central cavity of vesicles of the invention. Table 4 shows the formulas for these vesicles.

TABLE 4

|  | E | F | G |
|---|---|---|---|
| Glyceryl Distearate | 11.2 g |  | 4.35 g |
| Glycol Stearate |  | 7.5 g |  |
| POE10 Stearyl Alcohol | 5.6 g | 1.5 g | 2.2 g |
| Cholesterol | 2.8 g | 0.75 g | 1.1 g |
| Soybean Oil |  | 8.5 g |  |
| Vitamin E | 2.2 g |  |  |
| Levamisole Base |  | 4.63 g |  |
| Butter Flavor Oil |  |  | 20.0 g |
| Deionized Water | 78.2 g | 74.12 g | 72.35 g |

Formulation E uses glyceryl distearate, polyoxyethylene 10 stearyl alcohol, and cholesterol as the lipophilic phase which are blended at 70° C. to obtain a clear, homogeneous solution. The Vitamin E acetate was dissolved therein and the mixture was hydrated with 65° C. water using the NovaMix ™ machine as described in Example 2.

Formulation F used a levamisole base (a sheep dip) in soybean oil at 75° C. to form the water immiscible phase. The glycol stearate, polyoxyethylene stearyl alcohol and cholesterol were heated together at 75° C. to obtain a clear, homogeneous solution and the levamisole/soybean oil mixture was blended therewith. The deionize water was heated to approximately 65° C. and used as a hydrating solution for the lipids, again using the previously described NovaMix ™ machine.

In formulation G, the lipids and cholesterol were melted together at 75° C. and the butter oil dissolved therein. Again, the deionized water was heated to approximately 65° C. and used as a hydrating solution in a NovaMix ™ machine.

All these formulations form acceptable vesicles, showing the diversity of the present invention.

Example 5

This Example shows three different formulations for vesicles using retinoic acid, with both cationic and anionic vesicles. Table 5 lists the formulations for each vesicle.

TABLE 5

|  | H | I | J |
| --- | --- | --- | --- |
| Glyceryl Distearate | 9.4 g | | |
| Glycol Stearate | | 13.2 g | 13.2 g |
| Dimethyl Distearyl Ammonium Chloride | 0.3 g | | |
| Dimethyl Dicetyl Ammonium Chloride | | 0.6 g | |
| Sodium Oleate | | | 1.0 g |
| Petrolatum | 15.7 g | | |
| Paraffin Wax | 16.8 g | | |
| Soybean Oil | | 22.0 g | 22.0 g |
| Retinoic Acid | 0.25 g | 0.25 g | 0.25 g |
| Deionized Water | 56.55 g | 62.75 g | 63.35 g |

Formulation H uses the paraffin wax/petrolatum carrier for the retinoic acid, with the retinoic acid being dissolves in the carrier at approximately 65°–75° C. The lipophilic phase is formed of glyceryl distearate, cholesterol, and the dimethyl distearyl ammonium chloride. The carrier containing the retinoic acid is blended into the lipophilic phase and is hydrated with the deionized water using the NovaMix ™ machine as described in Example 2.

Formulations I and J use the soybean oil carrier and the same materials except for the secondary lipid. In formulation I, the secondary lipid, which forms part of the initial lipophilic phase, is dimethyl dicetyl ammonium chloride while in formulation J, the secondary lipid, which is incorporated into the aqueous phase, is sodium oleate. In either case, the retinoic acid is dissolved in the soybean oil at elevated temperatures, the soybean oil is blended into the lipophilic phase, and the combined phase is then hydrated using the aqueous phase. Formulation J forms anionic vesicles while formulation I forms cationic vesicles. However, both are effective in encapsulating the retinoic acid The foregoing Examples are merely illustrative and those skilled in the art may be able to determine other materials and methods and useful in the present invention. Such other materials and methods are encompassed within the following claims.

What is claimed is:

1. A lipid vesicle comprising at least two distinct lipids, a primary lipid and a secondary lipid, said primary lipid constituting the greatest proportion, by weight, of any single lipid material forming the bilayers of said vesicle, said primary lipid being selected from the group consisting of $C_{12}$–$C_{18}$ fatty alcohols, $C_{12}$–$C_{18}$ glycol monoesters, $C_{12}$–$C_{18}$ gyceryl mono-and diesters, and mixtures thereof, and said primary lipid further having the property that it will to form a lipid vesicle in the absence of said secondary lipid, and said secondary lipid being present in an amount sufficient to allow formation of said lipid vesicles, said secondary lipid being selected from the group consisting of quaternary dimethyldiacyl amines, polyoxyethylene acyl alcohols, polyglycerols, sorbitan fatty acid esters, fatty acids and their salts, and mixtures thereof.

2. The lipid vesicle of claim 1 wherein said primary lipid has the further property of not forming a lamellar phase in absence of said secondary lipid.

3. The lipid vesicle of claim 1 wherein said primary lipid is selected from the group consisting of $C_{16}$–$C_{18}$ fatty alcohols, glycol stearate, glyceryl mono- and distearate, glyceryl dilaurate, and mixtures thereof.

4. The lipid vesicle of claim 1 wherein said secondary lipid has the property that it will not form a vesicle in the absence of said primary lipid.

5. The lipid vesicle of claim 1 wherein said primary lipid and said secondary lipid have like chain length and unsaturation.

6. The lipid vesicle of claim 1 wherein said bilayer further comprises a sterol.

7. The lipid vesicle of claim 6 wherein said sterol is selected from the group consisting of cholesterol, salts and esters of cholesterol, phytocholesterol, hydrocortisone, and mixtures thereof.

8. The lipid vesicle of claim 1 wherein said lipid vesicle a paucilamellar lipid vesicle.

9. The lipid vesicle of claim 10 wherein said paucilamellar lipid vesicle comprises an amorphous central cavity containing a water immiscible material selected from the group consisting of mineral oils, paraffin waxes, petrolatum, triglyceride oils and fats, perfumes and fragrances, flavor oils, perfluorocarbon liquids, anthralin, retinoic acid, water insoluble vitamins, water immiscible solvents and mixtures thereof.

* * * * *